(12) United States Patent
Giorno

(10) Patent No.: US 7,670,142 B2
(45) Date of Patent: *Mar. 2, 2010

(54) PROSTHESIS MOUNTING DEVICE AND ASSEMBLY

(75) Inventor: Thierry Giorno, Boca Raton, FL (US)

(73) Assignee: Intra-Lock International, Inc., Boca Raton, FL (US)

( * ) Notice: Subject to any disclaimer, the term of this patent is extended or adjusted under 35 U.S.C. 154(b) by 186 days.

This patent is subject to a terminal disclaimer.

(21) Appl. No.: 11/739,343

(22) Filed: Apr. 24, 2007

(65) Prior Publication Data

US 2007/0190490 A1    Aug. 16, 2007

Related U.S. Application Data

(63) Continuation-in-part of application No. 10/453,309, filed on Jun. 3, 2003, now Pat. No. 7,217,130.

(51) Int. Cl.
*A61C 8/00* (2006.01)
(52) U.S. Cl. .................................. 433/213; 433/174
(58) Field of Classification Search ................ 433/173, 433/174, 206, 213
See application file for complete search history.

(56) References Cited

U.S. PATENT DOCUMENTS

| 3,466,748 A | | 9/1969 | Christensen |
| 4,193,194 A | | 3/1980 | Dalise |
| 4,202,101 A | | 5/1980 | Weissman |
| 4,575,340 A | * | 3/1986 | Lustig ........................... 433/173 |
| 4,728,292 A | | 3/1988 | Lustig et al. |
| 4,744,753 A | * | 5/1988 | Ross ............................. 433/173 |
| 4,767,332 A | | 8/1988 | Weissman |
| 4,826,434 A | | 5/1989 | Krueger |
| 5,049,072 A | | 9/1991 | Lueschen |
| 5,052,929 A | * | 10/1991 | Seal ............................. 433/173 |

(Continued)

FOREIGN PATENT DOCUMENTS

WO    WO 00/64369    11/2000

(Continued)

OTHER PUBLICATIONS

IMTEC Sendax Mini Dental Implant System (MDI), Small Wonder, 4-page color brochure.

(Continued)

*Primary Examiner*—Ralph A Lewis
(74) *Attorney, Agent, or Firm*—Reising Ethington P.C.

(57) ABSTRACT

A prosthesis mounting device and assembly for securing a prosthesis on an implant supported in bone tissue. An appendage or "preppable abutment" is carried by a dental implant and is milled or "prepped" into a shape suitable to accept a dental prosthesis such as a crown or bridge. Alternatively the appendage may be cast using a lost-wax investment molding process in which an appendage model is shaped by adding and sculpting wax onto portions of a calcinable appendage and/or removing material from portions of the appendage before using the model to form a mold. In each case the appendage is formed to include a recess that extends axially upwardly from a bottom end of the appendage and is shaped to fit over an O-ring receiver abutment or "O-ball" of a dental implant.

8 Claims, 12 Drawing Sheets

U.S. PATENT DOCUMENTS

| | | |
|---|---|---|
| 5,061,181 A | 10/1991 | Niznick |
| 5,078,606 A * | 1/1992 | Soderberg .................. 433/173 |
| 5,098,295 A | 3/1992 | Durr et al. |
| 5,180,303 A * | 1/1993 | Hornburg et al. ........... 433/173 |
| 5,205,745 A | 4/1993 | Kamiya et al. |
| 5,211,561 A | 5/1993 | Graub |
| 5,263,996 A | 11/1993 | Filhol |
| 5,312,255 A | 5/1994 | Bauer |
| 5,520,540 A | 5/1996 | Nardi et al. |
| 5,639,237 A | 6/1997 | Fontenot |
| 5,662,475 A | 9/1997 | Mena |
| 5,667,384 A * | 9/1997 | Sutter et al. ................. 433/172 |
| 5,704,788 A | 1/1998 | Milne |
| 5,749,732 A | 5/1998 | Sendax |
| 5,842,864 A | 12/1998 | Unger |
| 5,967,783 A | 10/1999 | Ura |
| 6,716,030 B1 | 4/2004 | Bulard et al. |
| 7,033,174 B2 * | 4/2006 | Giorno ....................... 433/174 |
| 7,217,130 B2 * | 5/2007 | Giorno ....................... 433/174 |
| 2004/0018471 A1 | 1/2004 | Giorno |

FOREIGN PATENT DOCUMENTS

| | | |
|---|---|---|
| WO | WO 01/12096 A1 | 2/2001 |
| WO | WO 03/103530 A1 | 12/2003 |

OTHER PUBLICATIONS

Dental Attachment Systems, The AIT Attachment for Retained Natural Tooth Roots, pp. 6 and 7.
Core-Vent Implant System, Core-Vent Corporation, 6 pages from catalog.
IMTEC Sendax MDI System, 5 pages of Product Description.

* cited by examiner

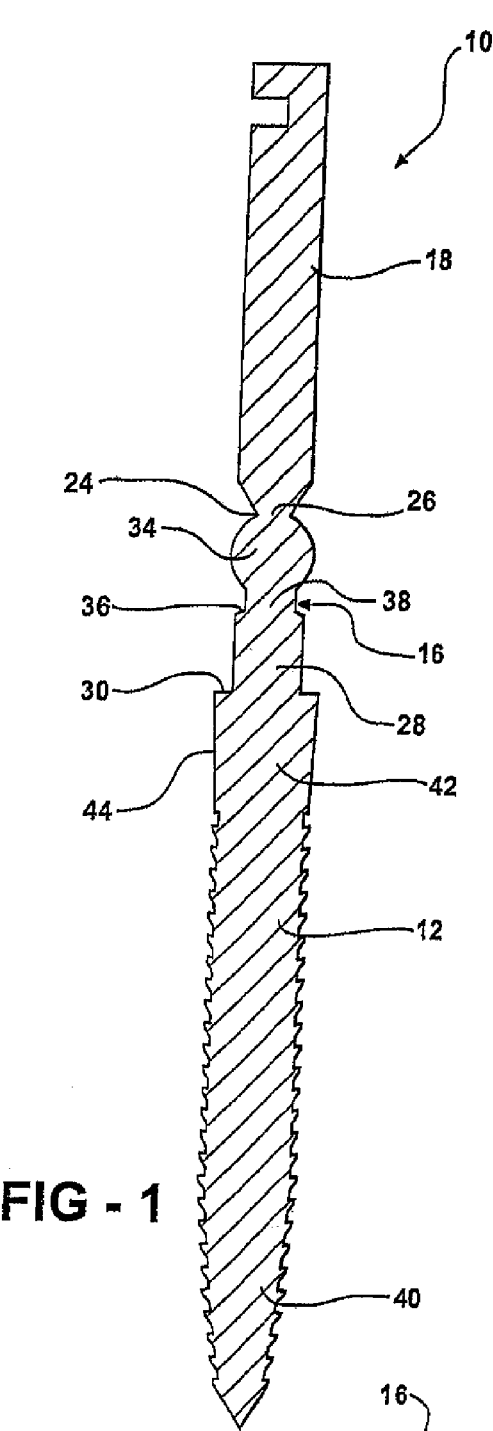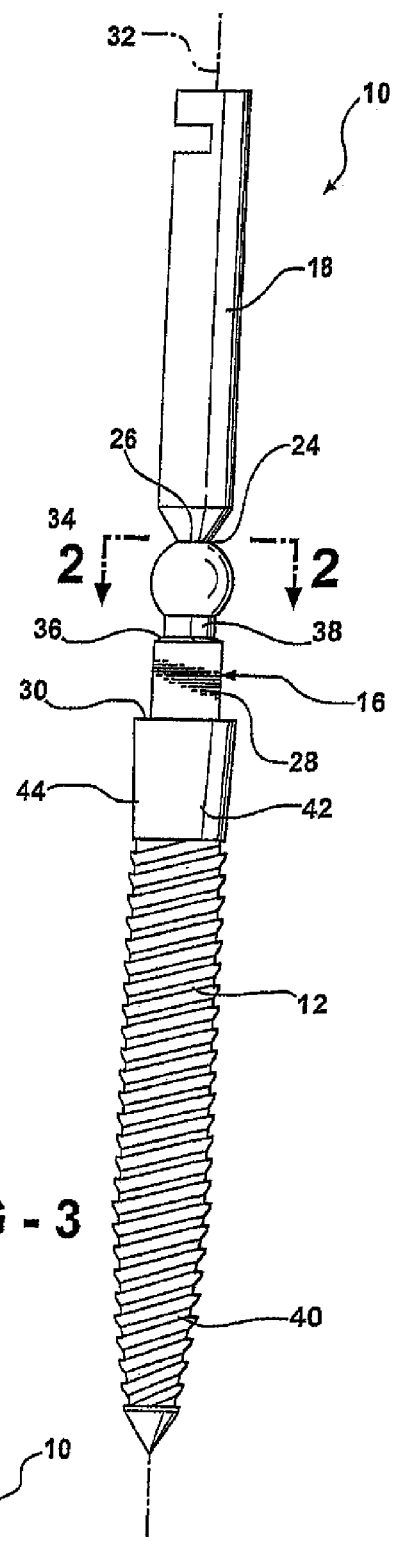
FIG - 1
FIG - 2
FIG - 3

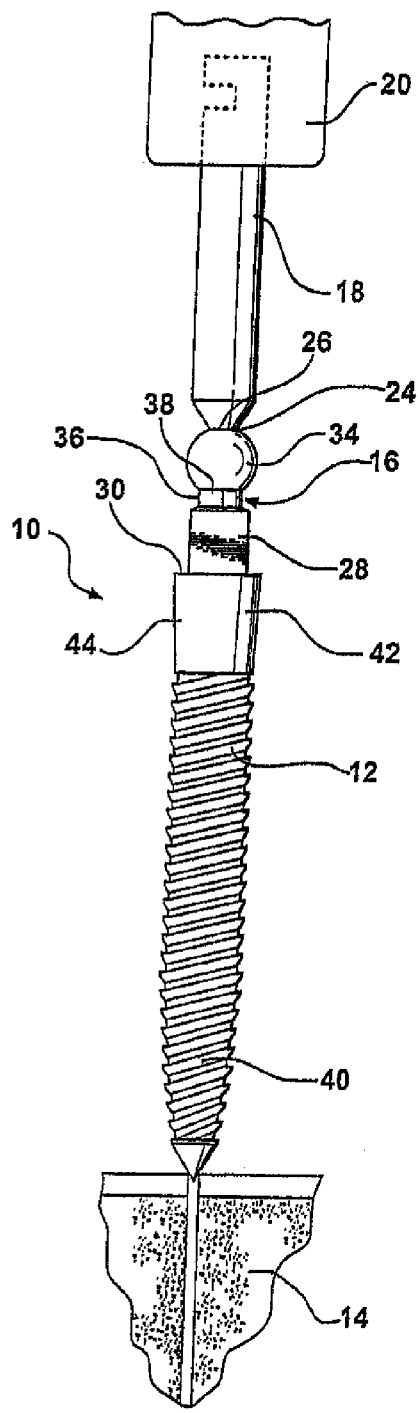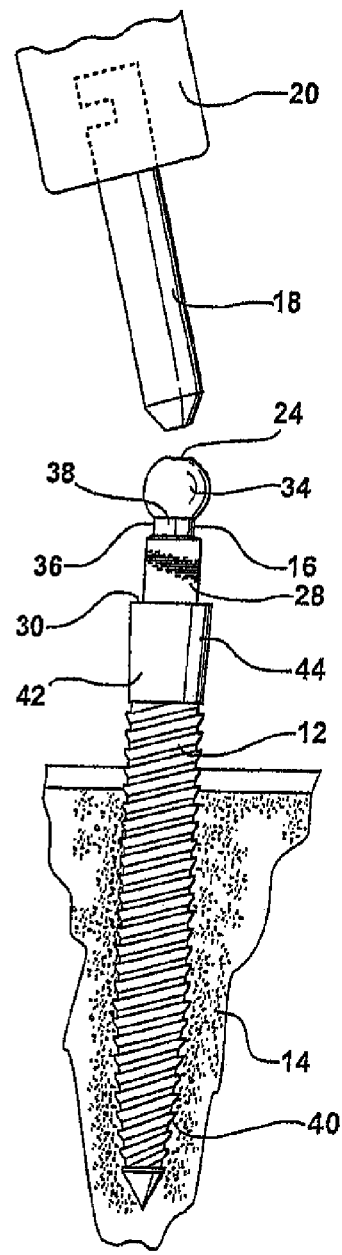
FIG - 4
FIG - 5

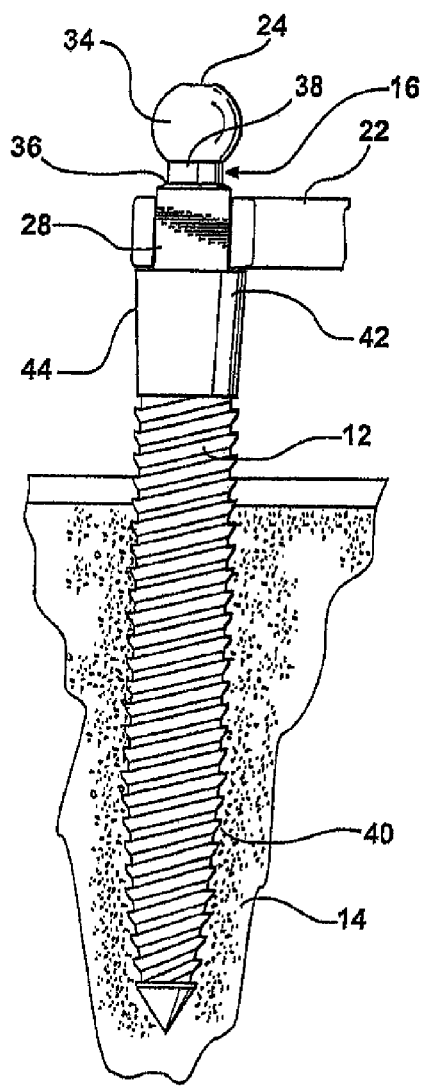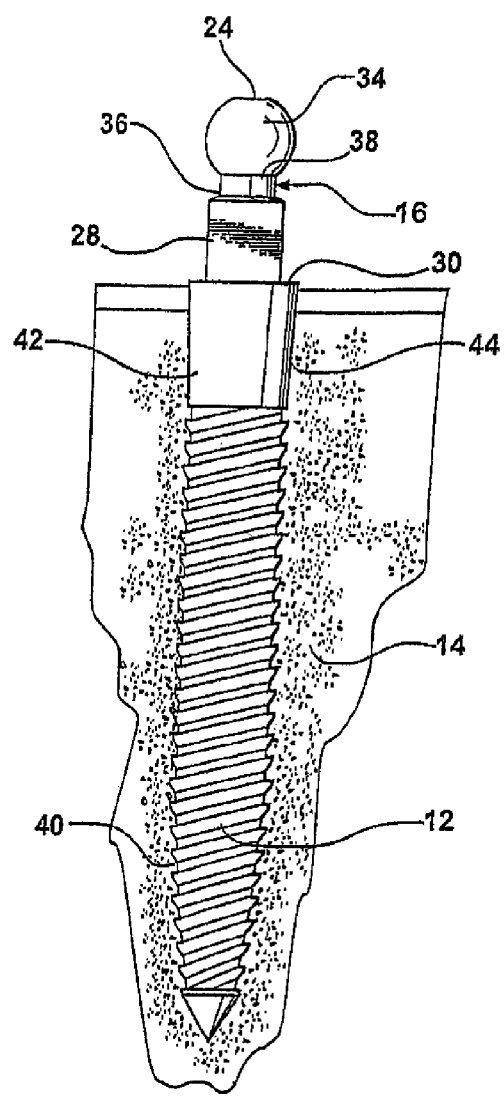
FIG - 6
FIG - 7

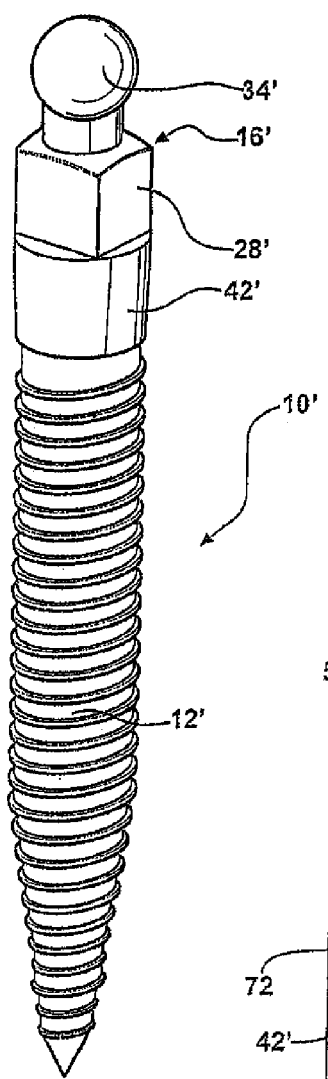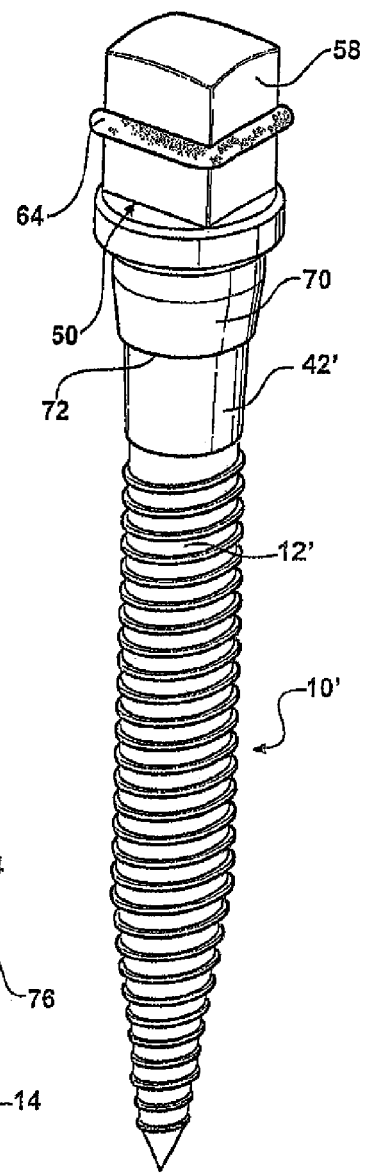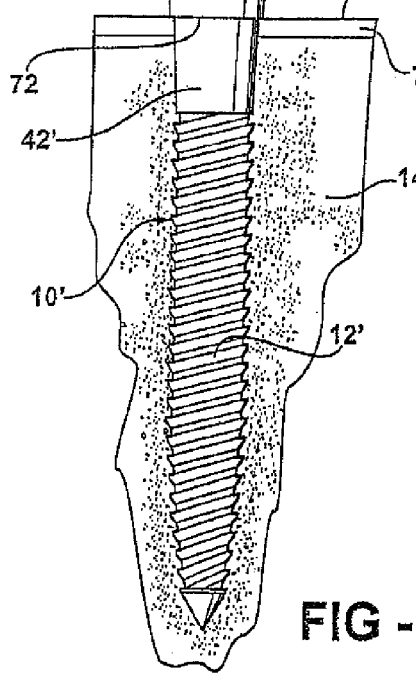
FIG - 8
FIG - 9
FIG - 10

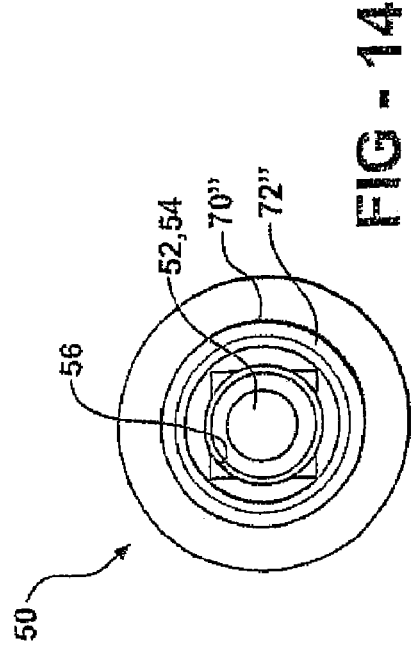
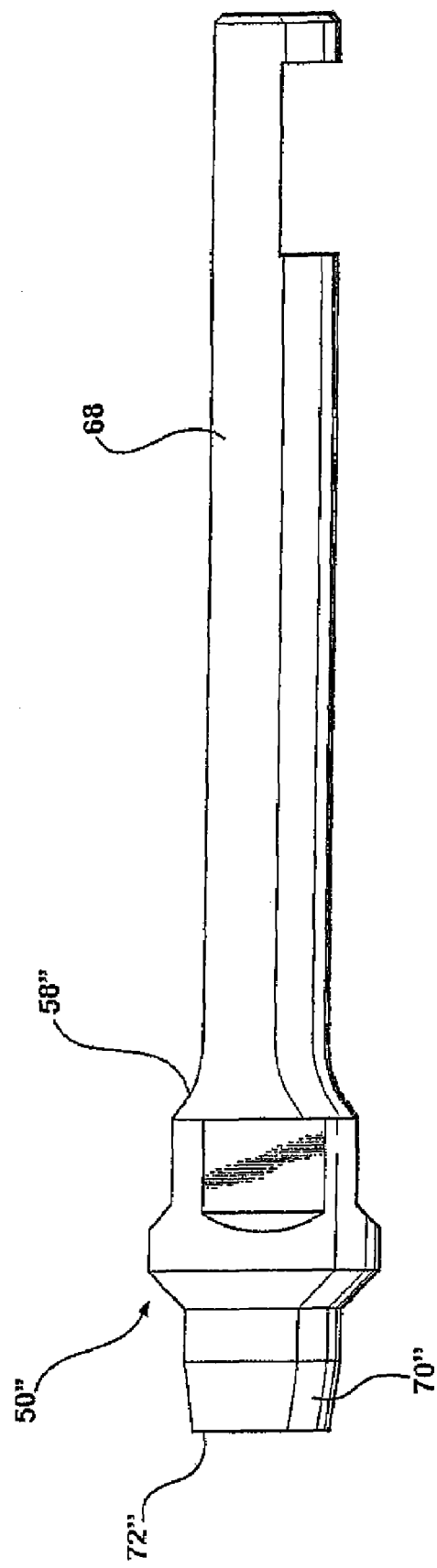

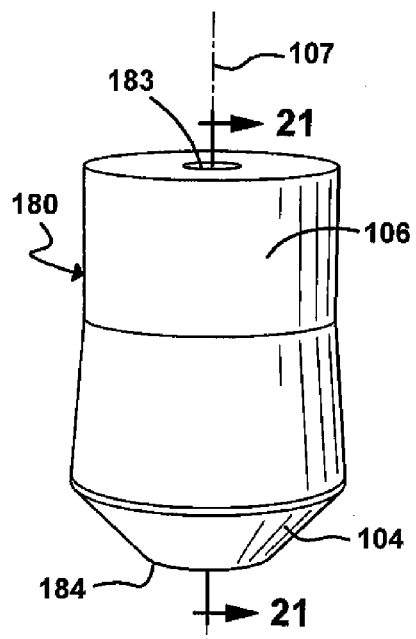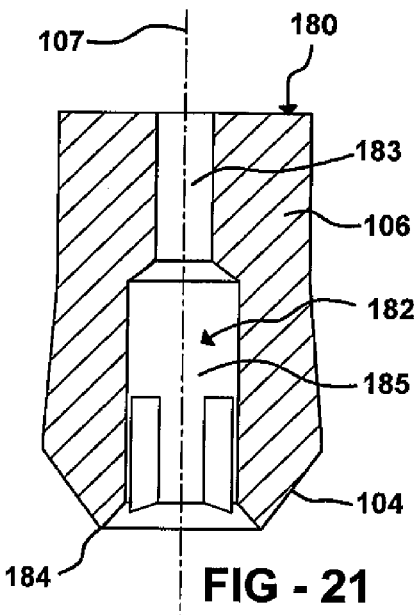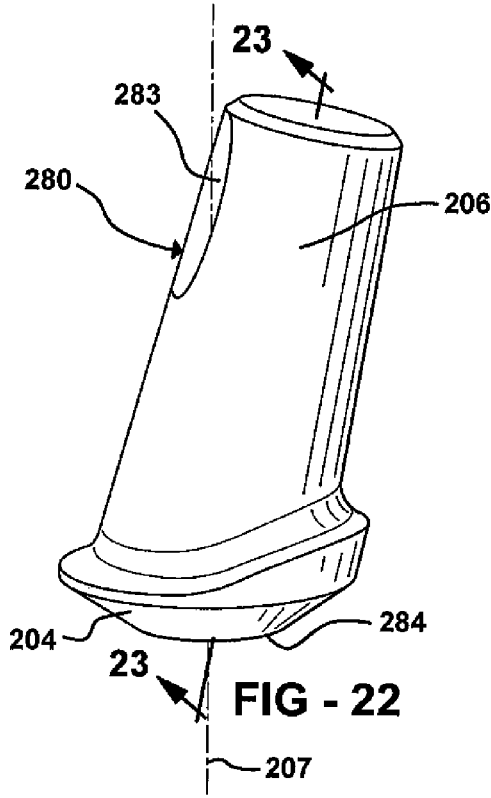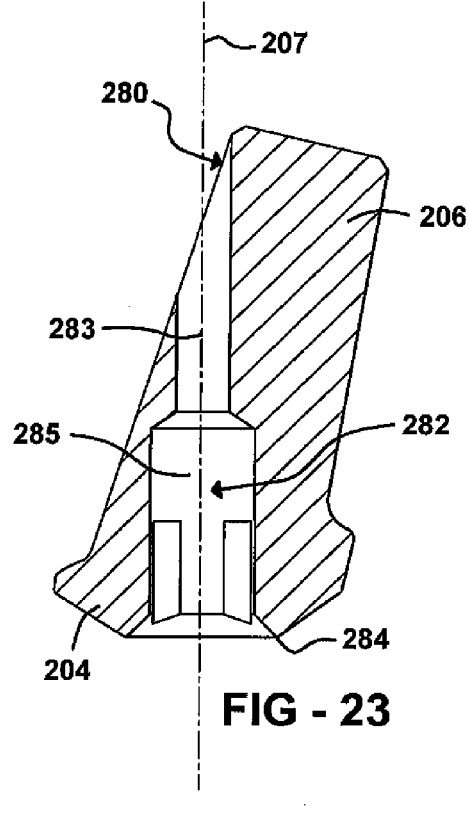

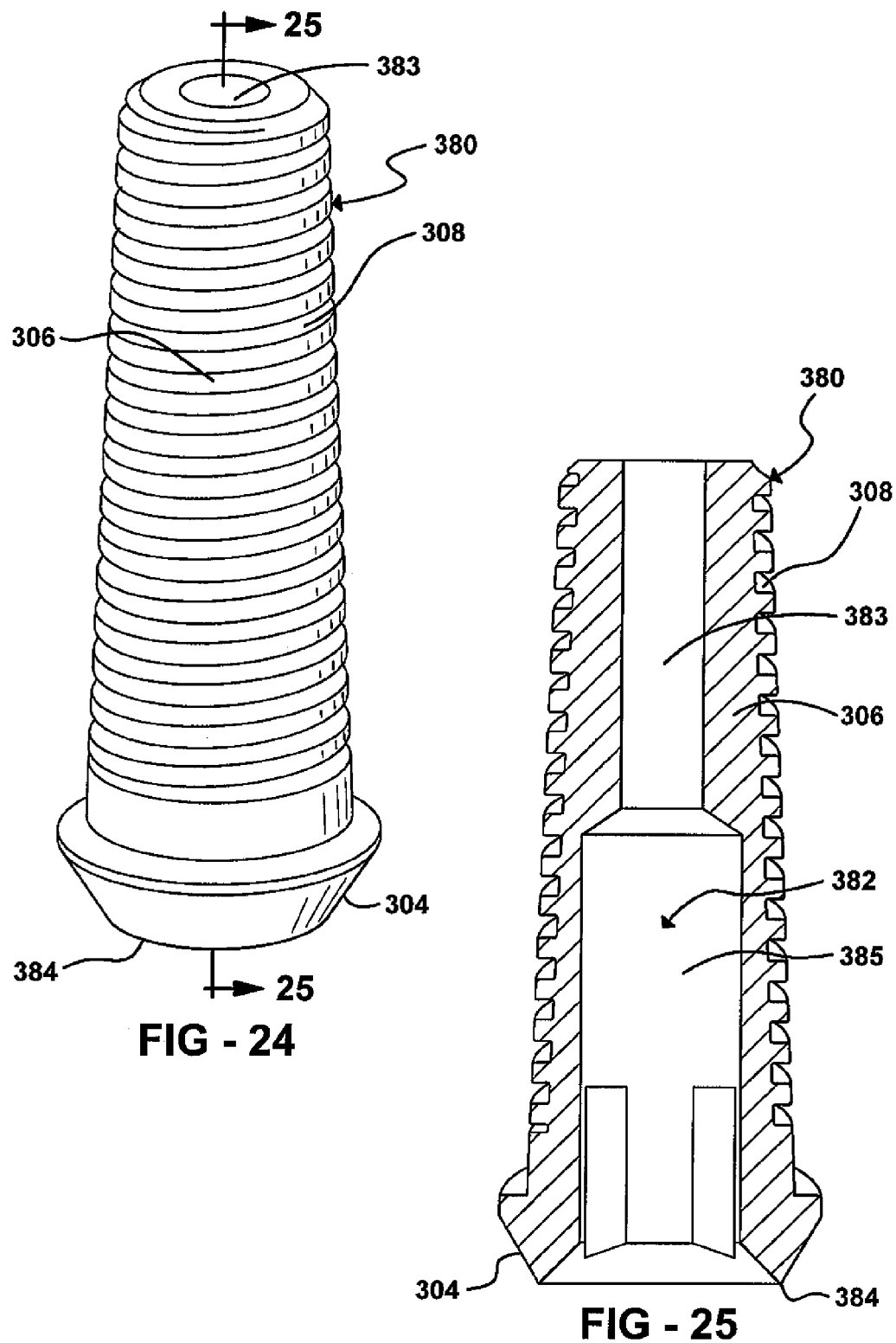

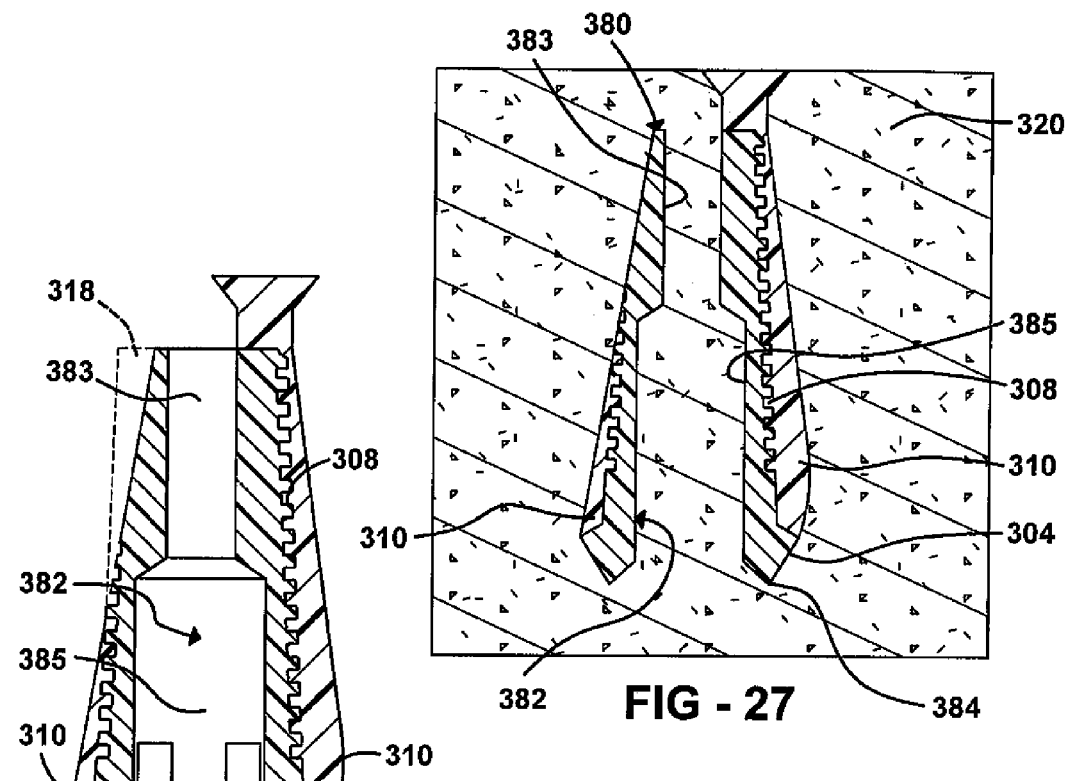
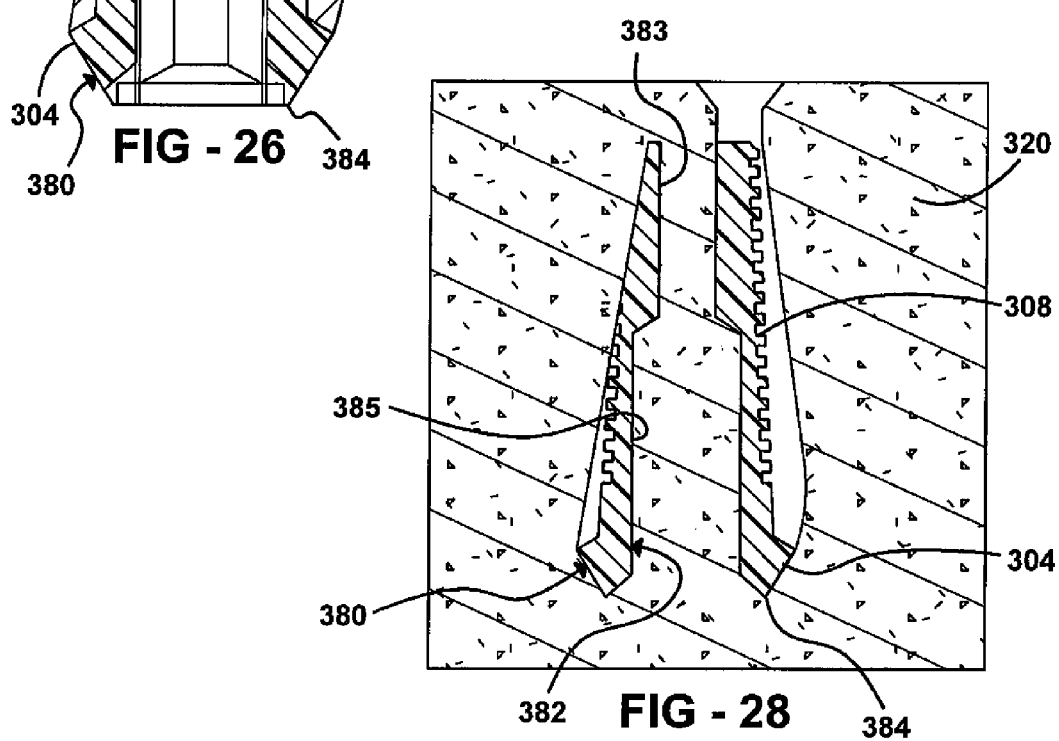

PROSTHESIS MOUNTING DEVICE AND ASSEMBLY

CROSS-REFERENCES TO RELATED APPLICATIONS

This application is a continuation-in-part application of Ser. No. 10/453,309, filed Jun. 3, 2003 now U.S. Pat. No. 7,217,130.

STATEMENT REGARDING FEDERALLY SPONSORED RESEARCH OR DEVELOPMENT

Not Applicable

BACKGROUND OF THE INVENTION

1. Field of the Invention

This invention relates generally to a prosthesis mounting device for securing a prosthesis on an implant supported in bone tissue.

2. Description of the Related Art Including Information Disclosed Under 37 CFR 1.97 and 1.98

Conventional dental prosthetics such as crowns, bridges and dentures have long been the standard prosthetic devices used to replace missing teeth. Such devices are secured to a jaw bone using a surgical anchor known as a dental implant or a prosthesis mounting device.

The design of dental implants has developed considerably over the years since their initial conception by the ancient Egyptians. One of the more important developments is credited to the Swedish firm, Noblepharma. In the mid-1980s, Noblepharma developed and marketed a dental implant that resembled a natural tooth root. This implant, known as a root form implant, include two major components: a bone screw and a prosthetic abutment interface. There are now about 10 major dental implant manufacturers in the United States alone that market various forms of the root form implant.

The protocol for surgical placement of a root form implant is to first expose an underlying jaw bone through a surgical intervention of the soft tissue covering the jaw bone. An opening is then created in the jaw bone equal to the minor diameter of the bone screw portion of the implant. This is done by using a series of expanding diameter surgical drills that allow the surgeon to gradually increase the size of the hole in the bone until the implant can be screwed into place. Once the implant has been screwed in, the soft tissue incision is sutured closed over the osteotomy site. In a process known in the art as osseointegration, the bone tissue around the device then grows into tight apposition to the screw during a three to six month healing process.

In recent years, however, some doctors have advocated what is known in the art as immediate or progressive loading of an implant. This process eliminates or shortens the time required for osseointegration and its associated long healing times. However, most implants still require that patients wait for an extended time before they can fully make use of permanent replacement teeth. Multiple surgeries are also required.

After a root form screw implant is firmly positioned in bone, and once the osseointegration process is complete, the tissue covering the osteotomy site is again reflected and an attachment device called an abutment is affixed to a head of the implant that remains exposed after installation. A dental prosthesis can then be cemented or screwed onto the prosthetic abutment portion of the implant. The prosthetic abutment portion of the device is available in many shapes, sizes and designs to accommodate various treatment applications.

Extending healing periods and costs associated with the above described two-stage surgical implant procedure have prevented traditional dental implant systems from becoming the chosen treatment modality for patients with missing teeth. Manufacturers and marketers of dental implants have been searching for new concepts and ideas that would provide a more economical and less surgically invasive system.

In response to this need, a New York City company called Dentatus® USA Ltd. began experimenting with endodontic posts designed to be implanted directly into a jaw bone. These endontic posts, known as MTI implants, had a one-piece design incorporating both screw and abutment. Because the diameter of the MTI implant was only 1.8 mm, Dentatus® was able to develop an implantation procedure that did not require a large opening in the bone to receive the implant. All that was necessary was a small, shallow starter hole that could be formed in jaw bone tissue directly through soft tissue without having to surgically lay back a flap of the soft tissue to expose the bone beneath. This new approach was minimally invasive and provided an implant that could be immediately loaded without having to wait for an extended period of time for osseointegration to occur. In the art, this new type of implant that's dimensionally small enough to self-tap into bone tissue without splitting the bone tissue became known as the mini dental implant.

While some standard sized (approx. 3.75 mm diameter) implants claim to be self-tapping, because of their larger size, the extent of their self-tapping is severely limited. Bone has a visco-elastic nature that allows it stretch, to a certain point, to accommodate inserted objects. However, to install an implant shaft larger than approximately 2.0 mm in diameter requires a large osteotomy formed by drilling progressively larger osteotomy holes to the full depth that the implant will extend into the bone. For example, a so-called self-tapping implant having a 3.75 mm diameter and 4.0 mm diameter threads will still require a 3.0 mm osteotomy. A cutter is supported near the tip of such an implant and extends radially outward to engage and form thread grooves in the wall of a 3.75 mm osteotomy as the implant is installed.

IMTEC® Corporation is currently marketing a Sendax mini dental implant system that comprises a prosthesis mounting device having a threaded shaft, and an abutment including a square nut and a ball-shaped O-ring abutment. The threaded shaft is tapered at a first end to allow the shaft to self-tap into bone tissue starting from a small, shallow pilot hole formed in bone tissue. Because the shaft self-taps past the depth of the pilot hole, it immediately integrates with the bone tissue. The square nut is attached to and extends integrally and axially from a second end of the threaded shaft opposite the first end. The O-ring abutment is attached to and extends integrally and axially from the square abutment. The O-ring abutment is shaped to engage and support a prosthetic tooth or set of teeth. However, this system is unable to disconnect or automatically discontinue torque application during installation when a predetermined bone density is encountered. Nor can such a device warn an installer that the bone tissue lacks sufficient density to properly support a prosthetic tooth. Still further, the Sendax mounting system cannot indicate to an installer when it is fully seated in bone tissue, the platform formed at the head area of the shaft is no greater than the cross-sectional area of the shaft itself and provides little support for a prosthesis, and it doesn't provide a satisfactory interface between the implant and surrounding soft tissues.

In implant dentistry, it is also known for a prosthesis mounting assembly to include a large titanium appendage or "preppable" abutment that detachably extends from an axial top surface of a full-sized dental implant or "tooth post". Such a preppable abutment is milled or "prepped", as a tooth would be prepped, into a generally triangular prism-like shape suitable to accept and support a crown or bridge. It's then fixed to the top surface of an implant using an axially-oriented prosthetic fixation screw. Typically, a preppable abutment of this type will also include either an internal or an external hex key or recess that engages a complementary recess or key formed on or in the axial top surface of an implant and the appendage may be milled either in the mouth of a model using a dentist's drill or by sending the preppable abutment to dental lab where a milling machine is used to prep the appendage.

In practice, an implant is first surgically installed by incising and laying back gum tissue to reveal jaw bone tissue, drilling a hole in the bone, inserting the implant, then closing the gum tissue over the osteotomy site and allowing oseointegration to occur. The preppable abutment is then installed on the implant by re-incising and laying back the gum tissue to reveal the axial top surface of the implant, positioning the preppable abutment on the implant, and fixing it in place with the prosthetic fixation screw. The gum tissue is then closed and allowed to heal. An impression is then taken of the preppable abutment and a coping is formed in the impression to duplicate the preppable abutment. The coping is used to form a stone model duplicating the patient's mouth. A prosthetic tooth or bridge is then formed on the stone model and coping to fit in the patient's mouth and over the preppable abutment extending upward from the embedded implant. Finally, the prosthetic tooth or bridge is supported on the preppable abutment. However, this type of preppable abutment requires an implant that is specifically configured to accept and support it. IN addition, this design is prone to micro movement that can but stress on and eventually break a prosthetic tooth or bridge.

What's needed is a prosthesis mounting device and assembly that doesn't require an implant that's specifically designed to support it.

BRIEF SUMMARY OF THE INVENTION

According to the invention, a prosthesis mounting assembly is provided for securing a prosthesis on an implant supported in bone tissue. The assembly comprises an implant including a threaded shaft configured to be screwed into bone tissue, an O-ring receiver abutment, and a multi-faceted integral nut attached to and axially extending from an aft end of the shaft. The assembly also comprises an appendage that's configured to be carried by the implant and that includes a recess extending into the appendage from a bottom end of the appendage. The recess includes an inner wall having a cylindrical portion shaped to engage and fit closely over the O-ring receiver abutment of the implant, and a multi-faceted portion shaped to engage and fit closely around the integral nut of the implant, forming an annular cavity between the recess wall and an undercut portion of the implant that is defined by a lower hemisphere of the O-ring receiver abutment of the implant.

Because the device fits over an O-ring receiver abutment, it allows for the manufacture of a single implant that can be used to support either a preppable abutment or a prosthetic having an O-ring interface. It also obviates the need for a surgical operation to install the preppable abutment on an implant after the implant has been installed. Also, a preppable abutment constructed according to the invention is able to function as an impression coping since it can come off in an impression tray. Still further, it can be secured in place on an implant without requiring a fixation screw.

Alternatively, according to the invention, the appendage may comprise calcinable material be configured to support the build-up and sculpting of material to obtain a desired shape to be invested to form a mold for casting a permanent appendage in a material suitable for supporting a dental prosthesis on the implant.

Further according to the invention a method is provided for securing a prosthesis on an implant supported in bone tissue. The method includes installing an implant in a patient's jaw bone, and removably supporting on the implant a calcinable appendage comprising calcinable material. The calcinable appendage is then sculpted into a desired dental prosthesis-supporting appendage shape by applying sculptable material to the calcinable appendage and shaping the sculptable material. An appendage mold is then formed by investing the sculpted appendage in refractory material and removing the sculpted appendage from the mold. A permanent appendage is then cast by providing suitable material in the mold, allowing the material to harden, and removing the refractory material from the hardened permanent appendage. The cast permanent appendage is then supported on the implant. A dental prosthesis is then molded to fit on the permanent appendage and is supported on the permanent appendage.

According to this method a permanent abutment may be cast in a more suitable shape for supporting a dental prosthesis since its shape may be augmented or added on to in whatever region of the appendage such augmentation might serve to better support a dental prosthesis.

BRIEF DESCRIPTION OF THE SEVERAL VIEWS OF THE DRAWINGS

These and other features and advantages of the invention will become apparent to those skilled in the art in connection with the following detailed description and drawings, in which:

FIG. 1 is a front view of a prosthesis mounting device constructed according to a first embodiment of the invention;

FIG. 2 is a cross-sectional front view of the device of FIG. 1;

FIG. 3 is a cross-sectional view of the device of FIG. 1 taken along line 2-2 in FIG. 1;

FIG. 4 is a front view of the prosthesis mounting device of FIG. 1 with a handle portion of the device connected to a rotary driver and a forward end of a threaded shaft portion of the device engaged in a small pilot hole formed in bone tissue;

FIG. 5 is a front view of the prosthesis mounting device of FIG. 4 with the handle portion of the device broken off and the threaded shaft portion of the device partially screwed into the bone tissue;

FIG. 6 is a front view of the prosthesis mounting device of FIGS. 4 and 5 with the handle portion removed and a ratchet wrench engaging a nut portion of an abutment of the device;

FIG. 7 is a front view of the prosthesis mounting device of FIGS. 4-6 shown after having been screwed into the bone tissue to a full desired depth;

FIG. 8 is a front isometric view of a prosthesis mounting device constructed according to a second embodiment of the invention;

FIG. 9 is an isometric view of a driver adapter supported on the mounting device of FIG. 8;

FIG. 10 is a front view of a ratchet wrench engaging the driver adapter of FIG. 9 and showing a threaded portion of the mounting device disposed in bone tissue;

FIG. 14 is an end view of the driver adapter of FIG. 9 showing an end opposite the end shown in FIG. 12; and FIG. 15 is a front view of an alternative driver adapter embodiment.

FIG. 20 is a perspective view of a first alternative appendage configuration;

FIG. 21 is a cross-sectional view of the appendage of FIG. 20 taken along line 21 of FIG. 20;

FIG. 22 is a perspective view of a second alternative appendage configuration;

FIG. 23 is a cross-sectional view of the appendage of FIG. 22 taken along line 23 of FIG. 22;

FIG. 24 is a perspective view of a third alternative appendage configuration;

FIG. 25 is a cross-sectional view of the appendage of FIG. 24 taken along line 25 of FIG. 24;

FIG. 26 is a cross-sectional view of the appendage of FIG. 24 showing a portion of the appendage that has been milled down and portions of the appendage that have been waxed-up to form a desired shape for a permanent appendage to be formed in a lost-wax investment molding procedure;

FIG. 27 is a cross-sectional view of the appendage of FIG. 26 invested in refractory material;

FIG. 28 is a cross-sectional view of the invested appendage of FIG. 27 showing a void left where the wax has been melted out;

DETAILED DESCRIPTION OF INVENTION EMBODIMENT(S)

Figure 11:
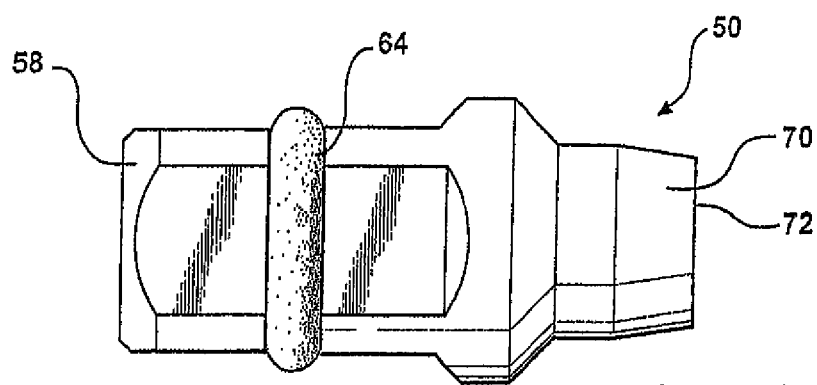
FIG. 11 is a front view of the driver adapter of FIG. 9.
Figure 12:
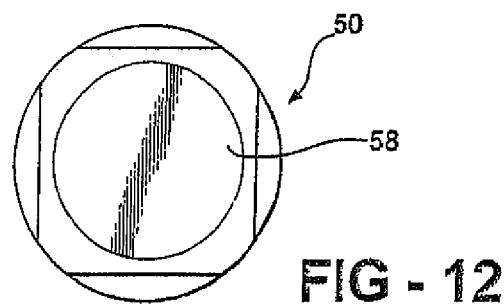
FIG. 12 is an end view of the driver adapter of FIG. 11.

A first embodiment of a prosthesis mounting device for securing a prosthesis such as a prosthetic tooth on bone tissue 14 is generally shown at 10 in FIGS. 1-7. A second embodiment is shown at 10' in FIGS. 9 and 10. Reference numerals with the designation prime (') in FIGS. 9 and 10, and in FIGS. 8 and 11-14, indicate alternative configurations of elements that also appear in the first embodiment. Unless indicated otherwise, where a portion of the following description uses a reference numeral to refer to the figures, that portion of the description is intended to apply equally to elements designated by primed numerals in FIGS. 8-14.

The device 10 includes a threaded shaft 12 or bone screw that is screwed into bone tissue 14 and a prosthetic abutment 16 attached to and axially extending from an aft end of the shaft 12. The abutment 16 engages and supports a prosthesis to serve as an interface between the prosthesis mounting device 10 and a prosthesis. The device 10 also includes an installation handle 18 connected to and extending axially from the abutment 16. The handle 18 is engaged and rotated by a manual or motor driven rotary driver 20 and is detached from the abutment 16 under a pre-determined torque load so that the handle 18 breaks off when bone tissue of a pre-determined density is encountered. This prevents an installer from continuing to use the rotary driver 20 when bone density requires that a different instrument, such as a ratchet wrench 22, be used for the remainder of the installation. Detachment of the handle 18 also indicates to an installer that bone tissue density is sufficient to support both initial and long-term stabilization of a prosthesis. If the handle 18 never breaks off during installation, the installer knows that bone tissue 14 density is insufficient to properly support a prosthesis.

The handle 18 extends from an aft end 24 of the abutment 16 from a weakened area 26 that defines an interface between the handle 18 and the abutment 16. This weakened area 26 is configured to break under a pre-determined torque load of approximately 30 Newton-centimeters (30 Ncm). The handle 18, abutment 16, and shaft 12 are integrally formed with one another as a single unitary piece. The weak area is a neck formed at the interface between the handle 18 and the abutment 16.

The handle 18 is a contra-angle post that can be engaged and rotated by a low speed contra-angle rotary driver 20. The contra-angle rotary driver 20 rotates the device 10 at a speed in the range of approximately 20-50 rpm.

The abutment 16 includes a nut 28 fixed to and axially extending from an aft end 30 of the threaded shaft 12. The nut 28 is shaped to be engaged and rotated by a tool adapted for that purpose. As best shown in FIG. 2, the nut 28 has a square cross section as measured perpendicular to a rotational axis 32 of the device 10. The nut 28 can be engaged and rotated by a ratchet wrench 22 or similar implement having a complimentary shaped engagement structure. In other embodiments, a nut and complimentary wrench of any other suitable configuration may be used instead of a square nut 28 and a wrench 22 with a square nut engagement box.

The abutment 16 also includes an O-ring abutment 34 fixed to and axially extending from an aft end 36 of the nut 28. The O-ring abutment 34 is an annular, generally spherical appendage known in the art as an "O-ball." The O-ring abutment 34 is designed to engage an O-ring disposed within a prosthesis according to any one of a number of different methods known in the art. The O-ring abutment 34 has a neck portion 38 where the O-ring abutment 34 merges with the aft end of the nut 28.

The threaded shaft 12 includes a tapered portion 40 shaped to wedge the shaft 12 into bone tissue 14 and instantly integrate with the bone tissue 14 upon installation. This increases initial stabilization and makes it possible to affix a permanent prosthesis to the O-ring abutment 34 immediately following installation.

The device 10 includes a collar 42 extending radially outward from around the aft end of the threaded shaft 12. The collar 42 is shaped to arrest threaded insertion of the device 10 at its proper depth. The shape of the collar 42 includes a frusto-conical surface 44 tapering radially outward and back from the threaded portion 12 of the shaft 12 to a point adjacent the aft end 30 of the shaft 12. Unlike the shaft 12, which has a relatively rough surface for bone integration, the collar is polished to promote adjacent soft tissue growth. The device 10 comprises a titanium alloy.

In practice, a device 10 constructed according to the first embodiment of the invention can be secured in bone tissue 14 by first transporting the device 10 in a sterile condition within a sterile package. When the time comes to install the device 10, the package is opened and a rotary driver 20 is connected to the handle 18. The rotary driver 20 is then used to withdraw the device 10 from the package and to transport the device 10 to the surgical site. The mounting device 10 is then screwed into bone tissue 14 by first engaging the threaded shaft 12 with a pilot hole formed into the bone tissue 14 through the soft tissue 14 covering the jaw bone as shown in FIG. 4. The rotary driver 20 is then operated to rotate the device 10 until the handle 18 either breaks off or the device 10 is fully seated to a pre-determined depth.

If bone density is sufficient to properly support the device 10 and an attached prosthesis, the handle 18 breaks off before the device 10 reaches its full pre-determined depth as shown in FIG. 5. The mounting device 10 is then screwed to its full desired depth in the bone tissue 14 as shown in FIG. 7. This is accomplished by engaging and rotating the prosthetic abutment 16 with a manual ratchet wrench 22 or similar implement as shown in FIG. 6.

If the handle 18 does not break off before the device 10 reaches its desired depth, the mounting device 10 is removed from the bone tissue 14 and an alternative prosthetic mounting method and/or device 10 more adaptable to supporting a prosthesis on soft bone tissue 14 is selected.

In addition to its breakaway feature, the installation handle 18 of the device 10 provides a hands-free delivery system. It allows a device 10 to be retrieved from a sterile container and transported to a surgical site without contaminating the portion of the shaft 12 to be implanted in bone tissue 14. The handle 18 also serves to transmit torque from a rotary driver 20 to the device 10 for threading the device 10 into bone tissue 14 without damaging the abutment 16. Abutment 16 damage can comprise secure attachment of a prosthesis to the device 10.

The device 10 is a "mini" dental implant dimensioned to self-tap into bone tissue starting at a small, approximately ¼" deep starter hole. The shaft portion 12 of the device 10 is approx. 1.8 mm in diameter. However, in other embodiments, the shaft may be up to approximately 2 mm in diameter depending on the visco-elastic properties of the bone.

The second prosthesis mounting device embodiment 10' is essentially identical to the first embodiment 10 except that the second embodiment includes no installation handle. Instead, as shown in FIG. 8, an O-ball 34' defines an upper end of the device 10'.

Figure 13:
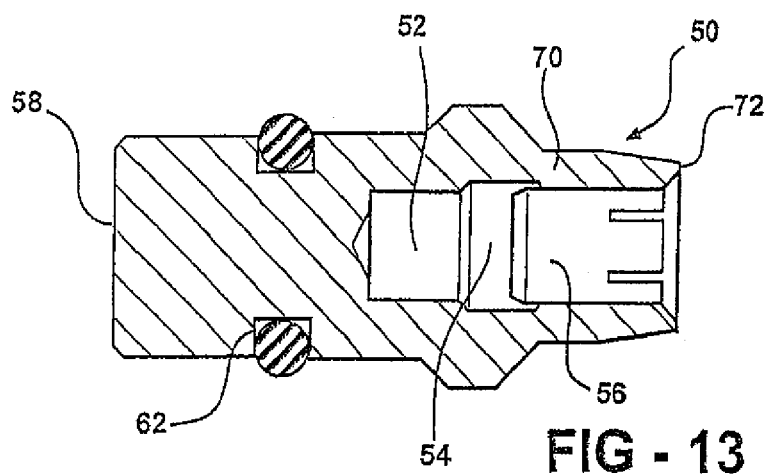
FIG. 13 is a cross-sectional front view of the driver adapter of FIG. 9.

Because the second mounting device embodiment 10' includes no integral installation handle, the invention also comprises a driver adapter 50 that receives the O-ball 34' and the square nut 28' into a complementary-shaped recess that's best shown at 52 in FIG. 13. An inner chamber 54 of the recess 52 is shaped to releasably retain the O-ball 34' in snap-fit fashion. An outer section 56 of the recess 52 is shaped to rotatably engage the nut when the O-ball 34' is fully received into the inner chamber 54.

An upper end 58 of the driver adapter 50 has a generally square cross-section shaped to be received into and rotatably engaged by a socket portion 60 a standard ratchet wrench 22' as shown in FIG. 10. A peripheral trench 62 is formed around the upper end 58 of the driver adapter 50 and a rubber O-ring 64 is received into the trench 62 as shown in FIGS. 9, 10, 12, and 13. The O-ring 64 provides an interference fit between the upper end 58 of the driver adapter 50 and an inner surface 66 of a ratchet wrench 22' that prevents the driver adapter 50 from falling out of a ratchet wrench 22' during transport to an osteotomy site. In other embodiments, such as the one shown in FIG. 15, a contra-angle drill adapter shaft 68 may be attached to or integrally formed with the driver adapter 50" and extend axially from the upper end 58" of the driver adapter 50". Such a contra-angle shaft would allow an installer to use a contra-angle drill to install the device. In either case, an installer can engage the mounting device 10', using either a ratchet wrench 22' or a contra-angle drill, and remove the device 10' from its sterile packaging without contaminating the device. The installer can then transport the mounting device 10' to an osteotomy site and install the device without ever touching or otherwise contaminating it.

Figure 17:
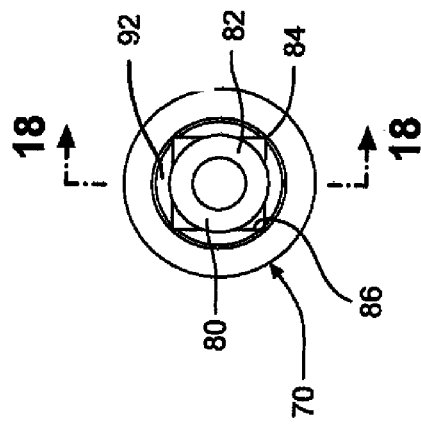
FIG. 17 is a right end view of the prosthesis mounting device of FIG. 16.
Figure 16:
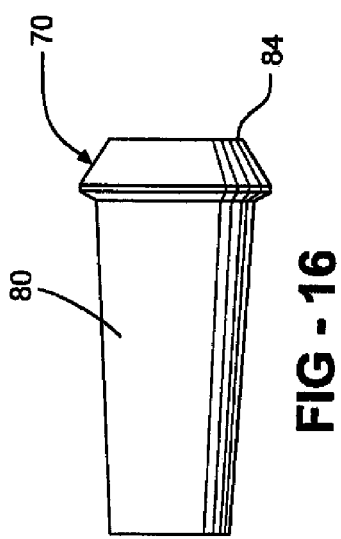
FIG. 16 is a side view of a prosthesis mounting device constructed according to the invention.
Figure 18:
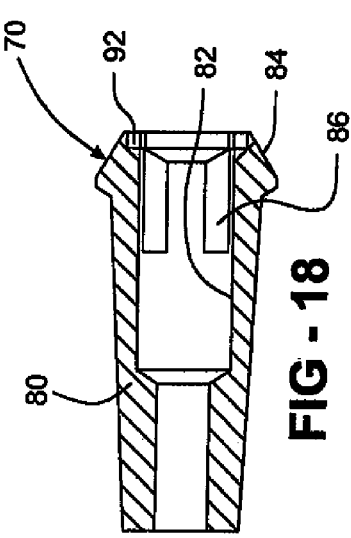
FIG. 18 is a cross-sectional side view of the prosthesis mounting device of FIGS. 16 and 17 and is taken along line 18-18 of FIG. 17.

A third embodiment of a prosthesis mounting device for securing a prosthesis on an implant supported in bone tissue is generally indicated at 70 in FIGS. 16-18. A prosthesis mounting assembly for securing a prosthesis on an implant supported in bone tissue is generally shown at 72 in FIG. 19 and includes the prosthesis mounting device 70 of FIGS. 16-18 and a miniature dental implant 74 having an O-ring receiver abutment 76 attached to and axially extending from an aft end of a threaded shaft 78 or bone screw.

The prosthesis mounting device 70 includes a titanium appendage or preppable abutment 80 that's shaped to be carried by a dental implant 74 or "tooth post". The preppable abutment 80 is milled, or "prepped", as a tooth would be prepped, into a generally triangular prism-like shape, or any other shape suitable to accept and carry a dental prosthesis such as a crown or a bridge. The device 70 also includes a recess 82 or axial channel that extends axially upwardly from an axial bottom end 84 of the preppable abutment 80. As is best shown in FIG. 19, the recess 82 is shaped to fit over an O-ball abutment or O-ring receiver abutment 76 of a miniature dental implant 74.

The recess 82 includes an axially lower portion 86 configured to engage a multi-faceted nut 88 of a dental implant 74 to limit rotation of a prosthetic relative to the preppable abutment 80. The axially lower portion 86 of the recess 82 is shaped to complement the shape of the multi-faceted nut 88 of the implant 74 to provide superior anti-rotation characteristics—as is particularly important in single-toothed prosthetic applications.

The recess 82 is shaped to fit closely over the O-ball receiver abutment 76 and the multi-faceted nut 88 of the implant 74 to minimize micro-movement between the preppable abutment 80 and the implant 74. In the present embodiment, the multi-faceted nut 88 has a square cross-section as measured perpendicular to a rotational axis of the device 70 and the recess 82 of the preppable abutment 80 has a generally square cross-section shaped to complement and receive the nut 88. In other embodiments, the nut 88 and recess 82 may have complementary cross-sectional shapes that are other than square.

Figure 19:
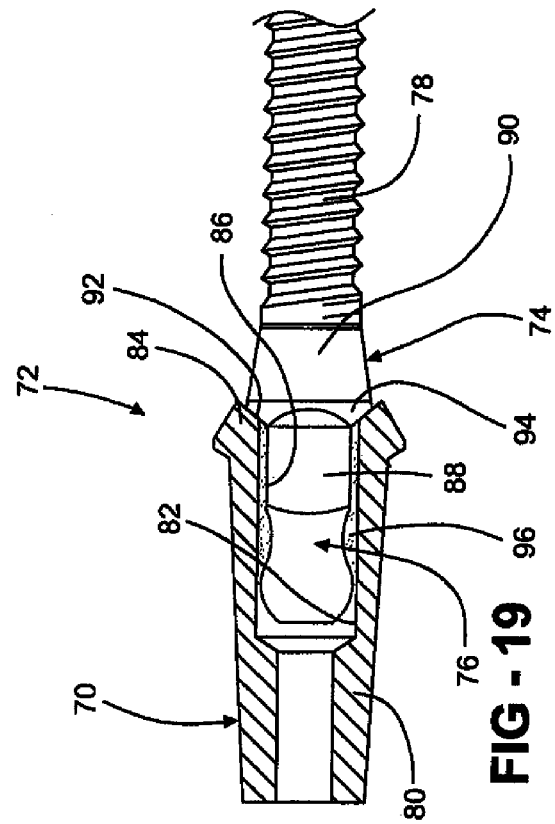
FIG. 19 is a partial cross-sectional side view of a prosthesis mounting assembly constructed according to the invention and showing the O-ring receiver abutment of an implant of the assembly received within the preppable abutment of FIGS. 16-18.

The recess 82 has an opening 92 shaped to receive a collar 90 that extends radially outward from around an aft end of the threaded shaft 78 of the implant 74 as best shown in FIG. 19. In the present embodiment, the opening 92 to the recess 82 has a frustoconical shape complimenting the shape of an upper, generally annular ramped surface 94 of the collar 90. This further secures the prosthesis mounting device 70 or preppable abutment 80 against micro-movement. As is also shown in FIG. 19, a layer of resin cement 96 bonds the O-ring receiver abutment 76 to the preppable abutment 80.

In practice, a prosthesis can be secured on an implant 74 supported in bone tissue by first installing one or more implants 74 in a patient's jaw bone within the patient's oral cavity, each implant 74 including an O-ring receiver abutment 76. The procedure for installing such an implant 74 is well-known in the art and is described in detail above. A preppable abutment 80 constructed according to the invention is then removably supported on each implant 74 by providing each preppable abutment 80 over a corresponding one of the O-ring receiver abutments 76 in respective positions for respective axially lower ends of the preppable abutments 80 engage respective upper surfaces 94 of the implant collars 90. The preppable abutments 80 are then prepped by milling each preppable abutment 80 as required to accommodate one or more dental prosthetics such as a bridge or respective prosthetic teeth. Each prepped abutment is milled to achieve parallelism, i.e., a parallel relationship between the surfaces of each preppable abutment 80, to provide a tighter fit over the O-ring receiver abutments 76 and a parallel relationship between the surfaces of adjacent preppable abutments 80 to allow a bridge to be slid over all the preppable abutments 80 along a single line of motion. The achievement of parallelism between abutments is important when multiple implants 74 and preppable abutments 80 are used. This is because, typically, every implant 74 is angled a little bit differently after it has been installed in bone tissue. The preppable abutments 80 are therefore machined in such a way as to correct for such differences in alignment or orientation.

One or more dental prosthetics are then formed to be supported on each of the preppable abutments 80. This is done by pressing an impression tray over each preppable abutment 80, and picking up each preppable abutment 80 in the impression tray such that the preppable abutments 80 serve as their own impression copings. An O-ball abutment analog is then inserted into each preppable abutment 80 carried in the impression tray. The O-ball abutment analogs are devices having the same size and shape as the O-ball abutments of the mini implants 74. Liquid casting material is then provided in the impression tray and allowed to harden into a model of the patient's teeth and gums in the vicinity of and surrounding the preppable abutments 80 and implants 74. The model is then removed from the impression tray and the preppable abutments 80 are also removed from the impression tray. The overall abutment analogs are then removed from each of the preppable abutments 80 and the preppable abutments 80 are then supported on the implants 74. The preppable abutments 80 are cemented onto the implants 74 with resin cement and then a metal reinforced bridge is cemented onto the preppable abutments 80.

A first alternative configuration of a prosthesis mounting assembly appendage is generally indicated at 180 in FIGS. 20 and 21, a second alternative appendage configuration is generally indicated at 280 in FIGS. 22 and 23, and a third alternative appendage configuration is generally indicated at 380 in FIGS. 24 and 25.

Each of the first, second, and third alternative appendage configurations 180, 280, 380 includes an implant receptacle or recess 182, 282, 382 extending upwardly into the appendage 180, 280, 380 from a bottom end 184, 284, 384 of the appendage 180, 280, 380 and may also include a passage or tunnel 183, 283, 383 extending through a top end of the appendage 180, 280, 380 forming a through-hole to allow for the escape of hydrostatic pressure. As is best shown representatively FIG. 32 with respect to the third alternative appendage configuration, the recess 182, 282, 382 includes an inner wall that may have a cylindrical portion 185, 285, 385 shaped to engage and fit closely over an O-ring receiver abutment 76 of a dental implant 74 and may also have a multi-faceted portion 186, 286, 386 shaped to engage and fit closely around an integral nut 88 of the implant 74, forming an annular cavity 390 between the recess wall 185, 285, 385 and an undercut portion of an implant 74 that is defined by a lower hemisphere of the O-ring receiver abutment 76 of the implant 74 and may be used to retain cement 96 in applications where the appendage 180, 280, 380 is to be permanently attached to an implant 74.

The first and second alternative appendage configurations 180, 280 are preppable abutments that fit over and engage the O-ring receiver abutments 76 of implants 74 and are configured to be milled into shapes suitable to accept and support prosthetic tooth bridges or crowns 302 on implants 74. The first and second alternative appendage configurations 180, 280 may comprise metal and may, more specifically, comprise titanium.

Also, each of the first and second and third alternative appendage configurations 180, 280, 380 may include an upwardly and outwardly tapered frusto-conical base 104, 204, 304 as shown in FIGS. 20-25. The tapered bases 104, 204, 304 allow the appendages 180, 280, 380 to accommodate prosthetic tooth crowns 302 of larger diameter or horizontal cross-sectional area.

According to the first alternative appendage configuration 180, and as shown in FIGS. 20 and 21, an upper portion 106 of the appendage 180 that extends upward from the base 104 may have a generally cylindrical or slightly upwardly and inwardly frustoconical shape oriented generally parallel to and distributed in a generally symmetric fashion about a recess axis 107 of the appendage 180. This appendage configuration 180 is optimized to support a prosthetic tooth crown or bridge in a desired attitude relative to a patient's jaw or mandible on an implant that has been installed so as to protrude from the jaw or mandible in the same general attitude as is desired for the tooth crown or bridge.

According to the second alternative appendage configuration 280, and as shown in FIGS. 22 and 23, a generally cylindrical or slightly upwardly and inwardly frustoconical shaped upper portion 206 of the appendage 280 that extends upward from its base 204 may be angled relative to a recess axis 207 of the appendage. This appendage configuration 280 is optimized to support a dental prosthesis such as a crown or bridge in a desired attitude relative to a patient's jaw or mandible on an implant that has been installed so as to protrude from the jaw or mandible at an angle or in an attitude significantly different from the attitude desired for the tooth crown or bridge.

According to the third alternative appendage configuration 380, and as shown in FIGS. 24 and 25, the appendage 380 comprises a calcinable material such as plastic, e.g. nyon, acetal, acrylic, or Delrin®, and is configured to support milling as well as the build-up and sculpting of a readily meltable and moldable material such as wax to obtain a desired shape to be invested to form a mold 320 for casting an appendage in a material suitable for supporting a prosthetic tooth crown on the implant 74 according to an investment or "lost wax" molding process. At least an upper portion 306 of the calcinable appendage 380 has a generally cone or frusto-conically-shaped exterior surface that may include an indentation 308 or surface irregularity to help retain sculpted meltable material 310 during wax-up and investment. As best shown in FIG. 24, the indentation 308 may take the form of a spiral groove winding around and extending along a portion of the frusto-conical exterior surface of the appendage 380.

Figures 31, 32:
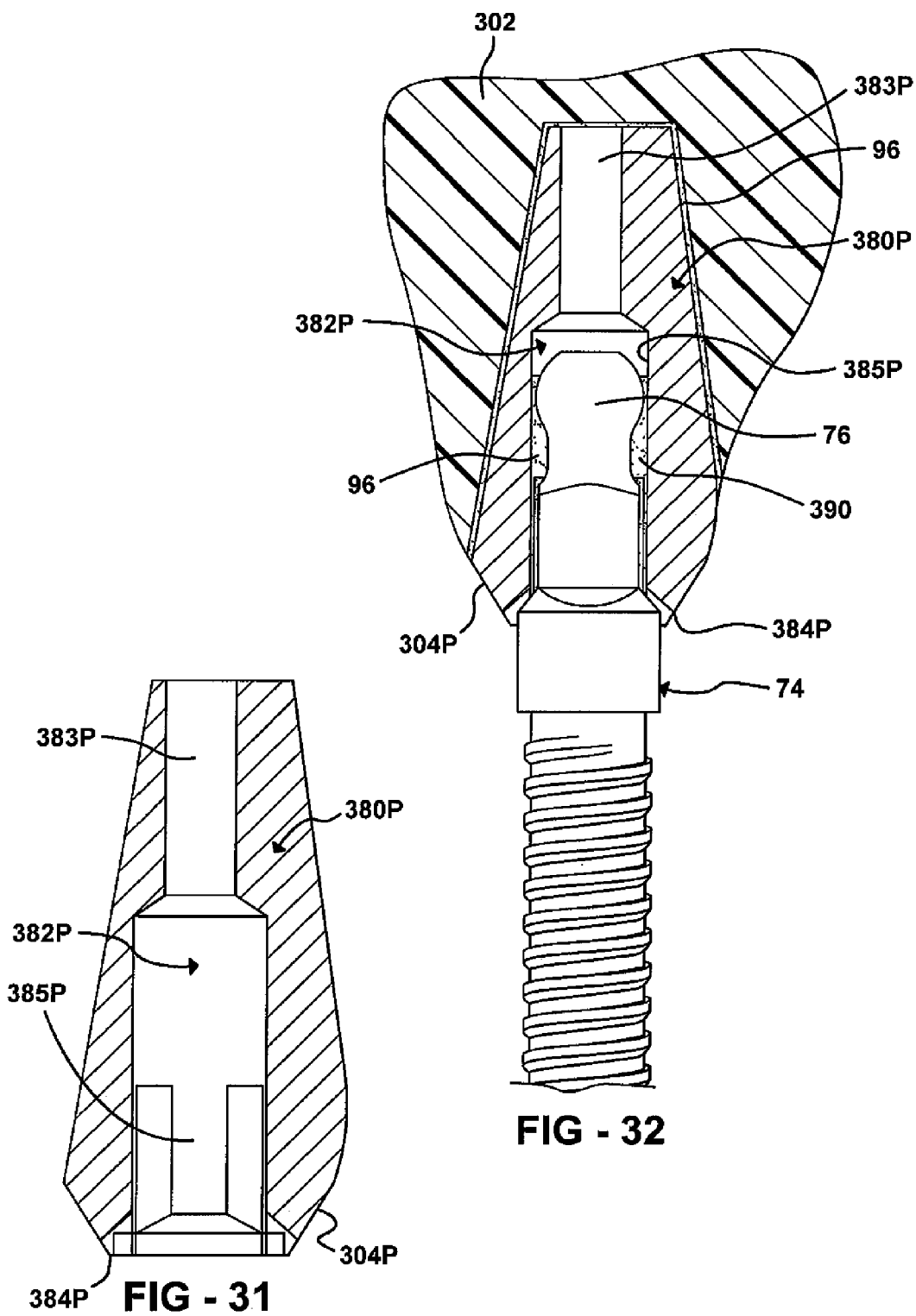
FIG. 31 is a cross-sectional view of the permanent appendage of FIG. 30 showing the refractory mold material having been removed.
FIG. 32 is a cross-sectional view of the permanent appendage of FIG. 31 shown permanently affixed to an implant and supporting a prosthetic dental crown on the implant.

As is representatively shown with regard to appendage 380P and implant 74 in FIG. 32, the appendage 180, 280,

380P may be molded to provide a gap between appendage recess 182, 282, 382P and the implant 74 sufficient to accommodate enough resin cement to prevent breakage of the resin cement, but small enough to preclude an unacceptable level of micromovement between the appendage 180, 280, 380P and the implant 74. This gap may fall within the range of 0.09 to 0.25 mm in width.

In practice, a dental prosthesis may be fabricated and secured on an implant 74 supported in bone tissue using an appendage constructed according to the third alternative appendage configuration 380 by first installing an implant 74 in a patient's jaw bone. An appendage 380 comprising calcinable material may then be removably supported on the implant 74. Where the installed implant 74 includes an O-ring receiver abutment 76 and an integral nut 88, the calcinable appendage 380 may include a receptacle 382 shaped to engage and fit closely over the O-ring receiver abutment 76 of the dental implant 74 and a multi-faceted portion 386 shaped to engage and fit closely around the integral nut 88 of the implant 74.

As shown in FIG. 26, a "waxed-up" model 312 of a permanent appendage having a desired shape for supporting a crown may then be sculpted on the calcinable appendage 380 by applying readily sculptable and meltable material 314 such as wax to the calcinable appendage 380 and shaping the scupltable material into a desired shape. Additional sculptable material 316 may then be added to the sculpted appendage model 312 in the shape of a mold access port. A desired crown-supporting shape may also be achieved by additionally removing material from the calcinable appendage by milling or other suitable means as shown in vacant region 318 of FIG. 26.

Figure 29:
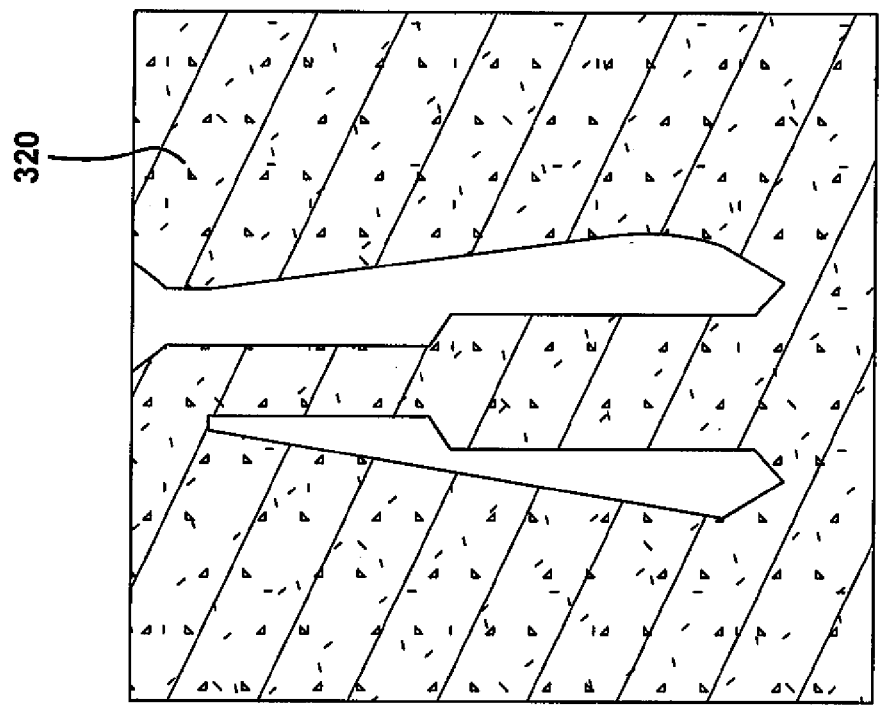
FIG. 29 is a cross-sectional view of the refractory material of FIG. 28 showing a void left where the wax has been melted out and where the appendage has been burned out.

As shown in FIG. 27, a mold 320 and mold access port 322 are then formed by investing in refractory material 324 the model comprising the calcinable appendage 380 and sculpted material 314, along with the material 316 that has been added and shaped to form a mold access port. The waxed-up model 312 (including the calcinable appendage 380 and added sculpted material 314) and added material 316 for an access port may then be removed from the mold 320 as shown in FIG. 28, by first melting the sculpted material 314 and added material 316 and draining it from the mold 320. As shown in FIG. 29, the calcinable material of the calcinable appendage 380 is then burned from the mold 320 according to any one of a number of suitable lost wax or investment molding methods as are well known in the art and are disclosed, for example, in U.S. Pat. Nos. 5,752,831; and 3,939,898; both of which are incorporated herein by reference.

Figure 30:
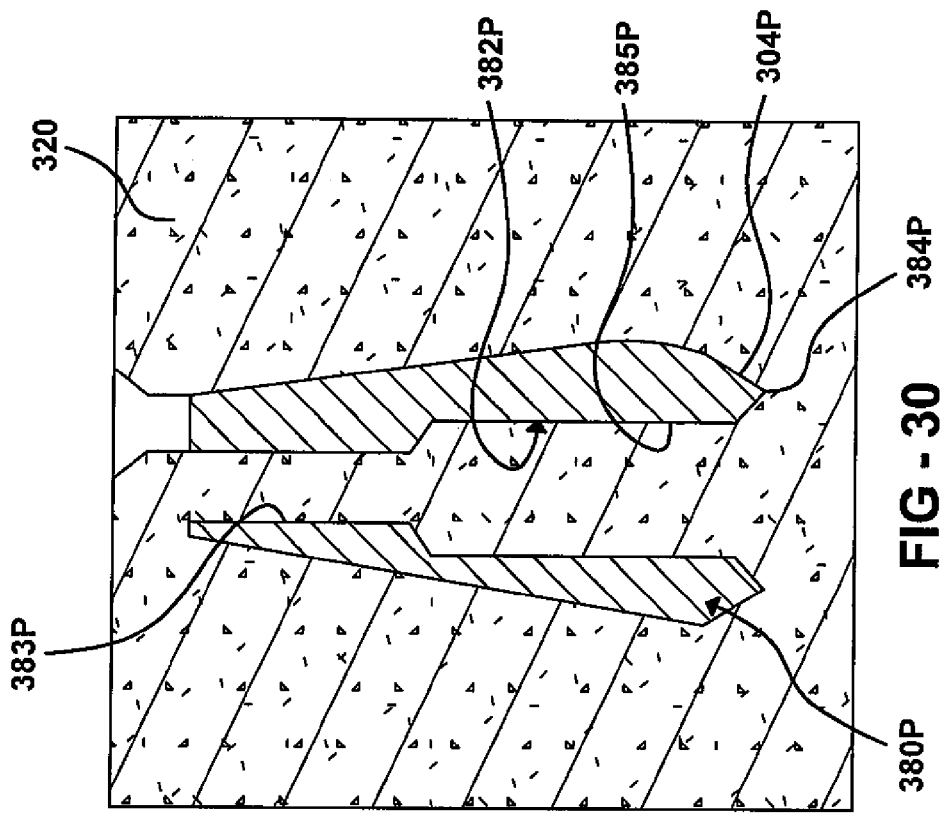
FIG. 30 is a cross-sectional view of the refractory mold of FIG. 29 showing molten metal having been poured into the mold to form a permanent appendage.

A permanent appendage 380P may then be formed by providing suitable appendage casting material 326 such as titanium, other suitable metals in the mold 320 as shown in FIG. 30, allowing the casting material 326 to cure or otherwise harden, and then removing the refractory material 324 from the hardened permanent appendage 380P as shown in FIG. 31, by sandblasting or any other suitable means known in the art. The provision of suitable appendage casting material 326 may, alternatively, include injecting and pressing a material comprising zirconium into the mold 320 through the mold access port 322 and then baking the material 326 according to a hot isostatic pressure (HIP) process as is well known in the art and disclosed in, for example, U.S. Pat. Nos. 4,954,080; 7,022,173; 6,984,261; and US Patent Application Publication Nos. 20050136176; 20050109060; 20050107491; and 20040152034, all of which are incorporated herein by reference.

A prosthetic tooth crown 330 may then be formed by impression molding or other suitable means to include a crown recess 332 that fits precisely over the permanent appendage 380P as shown in FIG. 32. The crown 330 may be permanently secured to the head of an implant 74 by first applying an adhesive 96 to either the head of the implant 74 or the recess 382P formed in the permanent appendage 380P and then supporting the permanent appendage 380P on the implant 74 by positioning the recess 382P of the permanent appendage 380P directly adjacent the head of the implant 74 and pushing the permanent appendage 380P onto the implant 74 such that the head of the implant 74 is received into the recess 382P. Second, an adhesive such as resin cement 96 may be applied either to the permanent appendage 380P or the crown recess 332 and the crown 330 positioned on the permanent appendage 380P such that the permanent appendage 380P is received into the crown recess 332.

According to this method a prosthetic tooth crown 330 can be supported on a permanent appendage 380P cast from a "waxed-up" model 312 that was sculpted while temporarily supported on an implant 74, with the permanent appendage 380P permanently mounted on that same implant 74 in precisely the same position as was the "waxed-up" model 312. This is because the recess 382P in the permanent appendage 380P will have the exact same shape and location in the permanent appendage 380P as did the recess 382 in the calcinable appendage 380.

This description, rather than describing limitations of an invention, only illustrates embodiments of the invention recited in the claims. The language of this description is therefore exclusively descriptive and is non-limiting. Obviously, it's possible to modify this invention from what the description teaches. Within the scope of the claims, one may practice the invention other than as described above.

What is claimed is:

1. A method for securing a prosthesis on an implant supported in bone tissue, the method including:
    installing in a patient's jaw bone an implant having an O-ball abutment and integral nut;
    removably supporting on the implant a calcinable appendage comprising calcinable material and having a receptacle shaped to engage and fit closely over the O-ball abutment of the implant and a multi-faceted portion shaped to engage and fit closely around the integral nut of the implant;
    sculpting the calcinable appendage into a desired permanent appendage shape by applying sculptable material to the calcinable appendage and shaping the sculptable material, the desired permanent appendage shape being suitable to allow a dental prosthesis to be supported on the permanent appendage after the permanent appendage has been formed;
    forming an appendage mold by investing the sculpted appendage in refractory material;
    removing the sculpted appendage from the mold;
    casting a permanent appendage by providing suitable material in the mold, allowing the material to harden, and removing the refractory material from the hardened permanent appendage;
    supporting the cast permanent appendage on the implant;
    molding a dental prosthesis to fit on the permanent appendage supported on the implant; and then
    supporting the dental prosthesis on the permanent appendage supported on the implant.

2. The method of claim 1 in which the step of sculpting the appendage into a desired dental prosthesis-supporting appendage shape includes applying wax to the appendage and shaping the wax to provide a desired dental prosthesis-supporting appendage shape.

3. The method of claim 2 in which:
the step of sculpting the appendage into a desired dental prosthesis-supporting appendage shape includes adding wax to the desired appendage shape in the shape of a mold access port; and
the investing step includes investing the added wax along with the sculpted appendage.

4. The method of claim 1 in which the step of sculpting the appendage into a desired dental prosthesis-supporting appendage shape includes removing material from portions of the appendage.

5. The method of claim 1 in which the step of removing the sculpted appendage from the mold includes melting the sculpted material and draining it from the mold.

6. The method of claim 1 in which the step of removing the sculpted appendage from the mold includes burning the calcinable material of the appendage from the mold.

7. The method of claim 1 in which the step of casting a permanent appendage includes providing a material comprising zirconium in a mold and then baking the material.

8. The method of claim 1 in which:
the step of removably supporting on the implant a calcinable appendage includes providing a calcinable appendage having a recess that extends upwardly into the appendage from an axial bottom end of the appendage, the recess including an inner wall having a cylindrical portion shaped to fit over the O-ball abutment of the implant and a multi-faceted portion shaped to engage and fit closely around the integral nut of the implant, forming an annular cement retention cavity between the recess wall and an undercut portion of the implant that is defined by a lower hemisphere of the O-ball abutment of the implant; and
the step of supporting the cast permanent appendage on the implant includes cementing the appendage on the implant such that cement is disposed within the cement retention cavity.

\* \* \* \* \*